(12) United States Patent
Proksa et al.

(10) Patent No.: US 7,668,289 B2
(45) Date of Patent: Feb. 23, 2010

(54) ENERGY-RESOLVED PHOTON COUNTING FOR CT

(75) Inventors: Roland Proksa, Hamburg (DE); Michael Grass, Buchholz in der Nordheide (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 91 days.

(21) Appl. No.: 11/912,689

(22) PCT Filed: Apr. 25, 2006

(86) PCT No.: PCT/IB2006/051285

§ 371 (c)(1),
(2), (4) Date: Oct. 26, 2007

(87) PCT Pub. No.: WO2006/117720

PCT Pub. Date: Nov. 9, 2006

(65) Prior Publication Data

US 2008/0205585 A1    Aug. 28, 2008

(30) Foreign Application Priority Data

Apr. 29, 2005    (EP)    .................. 05103589

(51) Int. Cl.
*A61B 6/03* (2006.01)
(52) U.S. Cl. .............................................. 378/19; 378/5
(58) Field of Classification Search .................... 378/5, 378/6, 19, 98.8, 98.9
See application file for complete search history.

(56) References Cited

U.S. PATENT DOCUMENTS

| 5,943,388 A | 8/1999 | Tumer |
| 2004/0129887 A1 | 7/2004 | Vydrin et al. |
| 2006/0056581 A1 * | 3/2006 | Hoffman et al. .............. 378/19 |

FOREIGN PATENT DOCUMENTS

| WO | 0222018 A2 | 3/2002 |
| WO | WO 2004002316 A1 * | 1/2004 |
| WO | 2004047140 A2 | 6/2004 |

* cited by examiner

*Primary Examiner*—Chih-Cheng G Kao

(57) ABSTRACT

Spectral CT systems require cheap detectors with high energy resolution. According to an aspect of the present invention, a computer tomography apparatus comprises a detector element which is segmented into a plurality of sub-pixels. Each sub-pixel has at least two thresholds and counting channels, wherein the second threshold for each sub-pixel varies over the nominal detector element. This may provide for an improved energy-resolved photon counting.

19 Claims, 3 Drawing Sheets

ENERGY-RESOLVED PHOTON COUNTING FOR CT

The present invention relates to the field of X-ray imaging. In particular, the present invention relates to a computer tomography apparatus for examination of an object of interest, to a detector for a computer tomography apparatus, to a method of examining an object of interest with a computer tomography apparatus, to a computer-readable medium and to a program element.

Over the past several years, X-ray baggage inspections have evolved from simple X-ray imaging systems that were completely dependent on interaction by an operator to more sophisticated automatic systems that can automatically recognize certain types of materials and trigger an alarm in the presence of dangerous materials. An inspection system has employed an X-ray radiation source for emitting X-rays which are transmitted through or scattered from the examined package to a detector.

Computed Tomography (CT) is a process of using digital processing to generate a three-dimensional image of the internals of an object from a series of two-dimensional X-ray images taken around a single axis of rotation. The reconstruction of CT images can be done by applying appropriate algorithms. An imaging technique based on coherently scattered X-ray photons or quanta is the so-called Coherent Scatter Computer Tomography (CSCT). CSCT is a technique that produces images of (particularly the low angle) scatter properties of an object of interest. These depend on the molecular structure of the object, making it possible to produce material-specific maps of each component. The dominant component of low angle scatter is coherent scatter. Since coherent scatter spectra depend on the atomic arrangement of the scattering sample, coherent scatter computer tomography is a sensitive technique for imaging spatial variations in the molecular structure of baggage or of biology tissue across a two-dimensional object section.

Photon counting detectors for CT or CSCT must support high counting rates. Spectral CT systems require cheap detectors with high energy resolution.

It may be desirable to have an improved energy-resolved photon counting detector for CT/CSCT systems.

According to the present invention, a computer tomography apparatus for examination of an object of interest may be provided, the computer tomography apparatus comprising a detector element segmented into a plurality of sub-pixels, wherein the plurality of sub-pixels comprises a first sub-pixel and a second sub-pixel. The first sub-pixel comprises a first counting channel corresponding to a first energy threshold and a second counting channel corresponding to a second energy threshold. The second sub-pixel comprises a third counting channel corresponding to a third energy threshold and a fourth counting channel corresponding to a fourth energy threshold.

According to the present invention, the computer tomography apparatus comprises a detector element sub-divided into single radiation detecting pixels each having a plurality of counting channels and energy thresholds. This may provide for high energy resolution at minimal effort.

Exemplary embodiment of the invention are disclosed in the dependent claims.

According to an exemplary embodiment of the present invention, the first sub-pixel is adapted for detecting a first radiation with a first energy above the first energy threshold and for detecting a second radiation with a second energy above the second energy threshold, resulting in first and second detection data. Furthermore, the second sub-pixel is adapted for detecting a third radiation with a third energy above the third energy threshold and for detecting a fourth radiation with a fourth energy above the fourth energy threshold, resulting in third and fourth detection data.

Therefore, each sub-pixel may detect two different types of radiation, the first type with a lower energy and the second type with a higher energy.

According to another exemplary embodiment of the present invention, the first counting channel is adapted for counting, as first counts, detection events resulting from photons with an energy above the first threshold energy, wherein the second counting channel is adapted for counting, as second counts, detection events resulting from photons with an energy above the second threshold energy. Furthermore, the third counting channel is adapted for counting, as third counts, detection events resulting from photons with an energy above the third threshold energy and wherein the fourth counting channel is adapted for counting, as fourth counts, detection events resulting from photons with an energy above the fourth threshold energy.

Therefore, each sub-pixel may count detection events corresponding to radiation with an energy above a predetermined threshold value and may (separately) count detection events corresponding to radiation with an energy above another, different, for example predetermined threshold value.

According to another exemplary embodiment of the present invention, the first threshold value or threshold energy equals the third threshold energy and the second threshold energy is different from the fourth threshold energy.

Therefore, the first sub-pixel may count different detection events than the second sub-pixel.

According to another exemplary embodiment of the present invention, the computer tomography apparatus further comprises a determination unit, which is adapted for combining the first, second, third and fourth detection data, resulting in an energy resolved result signal representing a nominal detection element.

According to another exemplary embodiment of the present invention, the result signal is represented on the basis of a first, second, third and fourth energy bin, wherein the first, second, third and fourth energy bins are discrete energy bins. Furthermore, the first and third threshold energies of the first and second sub-pixel are lower than the second threshold energy which again is lower than the fourth threshold energy. The third counts, resulting from photons with an energy above the third threshold energy, are equally distributed into the third and fourth energy bins.

This may provide for an analysis of the detection data on the basis of energetic considerations.

According to another exemplary embodiment of the present invention, the first and second sub-pixels are adapted for detecting corresponding single photons.

Therefore, photons may individually be counted and the respective counted numbers may be used for a following energy-resolved analysis of the detection data. Counting single photons may result in a high energy resolution and sensitivity.

According to another exemplary embodiment of the present invention, the computer tomography apparatus is adapted as a coherent scatter computer tomography apparatus.

The computer tomography apparatus may comprise an electromagnetic radiation source adapted for emitting electromagnetic radiation to the object of interest and a collimator arranged between the electromagnetic radiation source and the detecting elements, wherein the collimator is adapted for collimating an electromagnetic radiation beam emitted by the electromagnetic radiation source to form a fan-beam or a cone-beam, or a beam of any other desired geometry. The detecting elements of the computer tomography apparatus may form a single-slice detector array, or alternatively a multi-slice detector array. The single-slice detector array may have the advantage of a simple configuration and a fast evaluation of the detected signals. However, a multi-slice detector array may be implemented to achieve a particularly high resolution of the detected signals, and a high amount of detected signals.

It should be noted, that the method of the invention may be valid for any trajectory, detector shape, beam geometry (e.g. fan-beam, cone-beam, etc.), and that it may support an energy-dependent attenuation map.

The computer tomography apparatus according to the invention may be applied as a baggage inspection apparatus, a medical application apparatus, a material testing apparatus or a material science analysis apparatus. A preferred field of application of the invention may be baggage inspection, since the defined functionality of the invention allows for a secure and reliable analysis of the content of a baggage item allowing to detect suspicious content, even allowing to determine the type of a material inside such a baggage item.

Such an apparatus or method in accordance with an exemplary embodiment of the present invention may create a high quality automatic system that may automatically recognize certain types of materials and, if desired, trigger an alarm in the presence of dangerous material. Such an inspection system may have employed the computer tomography apparatus of the invention with an X-ray radiation source for emitting X-rays which are transmitted through or scattered from the examined package to a detector allowing to detect coherently scattered radiation in an energy-resolved manner.

Furthermore, according to another exemplary embodiment of the present invention, a detector for a computer tomography apparatus for examination of an object of interest is provided, the detector comprising a detector element segmented into a plurality of sub-pixels. Such a detector may be implemented into the computer tomography apparatus mentioned above.

According to another exemplary embodiment of the present invention, a method of examining an object of interest with a computer tomography apparatus is provided, the method comprising the steps of detecting, by a first sub-pixel, a first radiation with a first energy above a first energy threshold and a second radiation with a second energy above a second energy threshold, resulting in first and second detection data, and detecting, by a second sub-pixel, a third radiation and a fourth radiation, wherein the third radiation has an energy above a third energy threshold and the fourth radiation has an energy above a fourth energy threshold, resulting in third and fourth detection data. Furthermore, the first sub-pixel comprises a first counting channel corresponding to the first energy threshold and a second counting channel corresponding to the second energy threshold. The second sub-pixel comprises a third counting channel corresponding to the third energy threshold and a fourth counting channel corresponding to the fourth energy threshold.

It is believed that this may allow for an improved energy-resolved photon counting for CT/CSCT applications.

According to another exemplary embodiment of the present invention, a computer-readable medium may be provided, in which a computer program of examining an object of interest with a computer tomography apparatus is stored which, when being executed by a processor, is adapted to carry out the above-mentioned method steps. Furthermore, a program element of examining an object of interest may be provided, which, when being executed by a processor, is adapted to carry out the above-mentioned method steps.

The examination of the object of interest according to the invention may be realized by the computer program, i.e. by software, or by using one or more special electronic optimization circuits, i.e. in hardware, or in hybrid form, i.e. by means of software components and hardware components.

It may be seen as the gist of an exemplary embodiment of the present invention that energy-resolved photon counting detectors are used which are segmented into individual sub-pixels, wherein each sub-pixel has at least two thresholds and counting channels. According to an exemplary embodiment of the present invention, the second threshold for each sub-pixel varies over the nominal detector cell.

These and other aspects of the present invention will become readily apparent from and elucidated with reference to the embodiments described hereinafter.

Exemplary embodiments of the present invention will be described in the following, with reference to the following drawings.

The illustration in the drawings is schematically. In different drawings, similar or identical elements are provided with the same reference signs.

Figure 1:
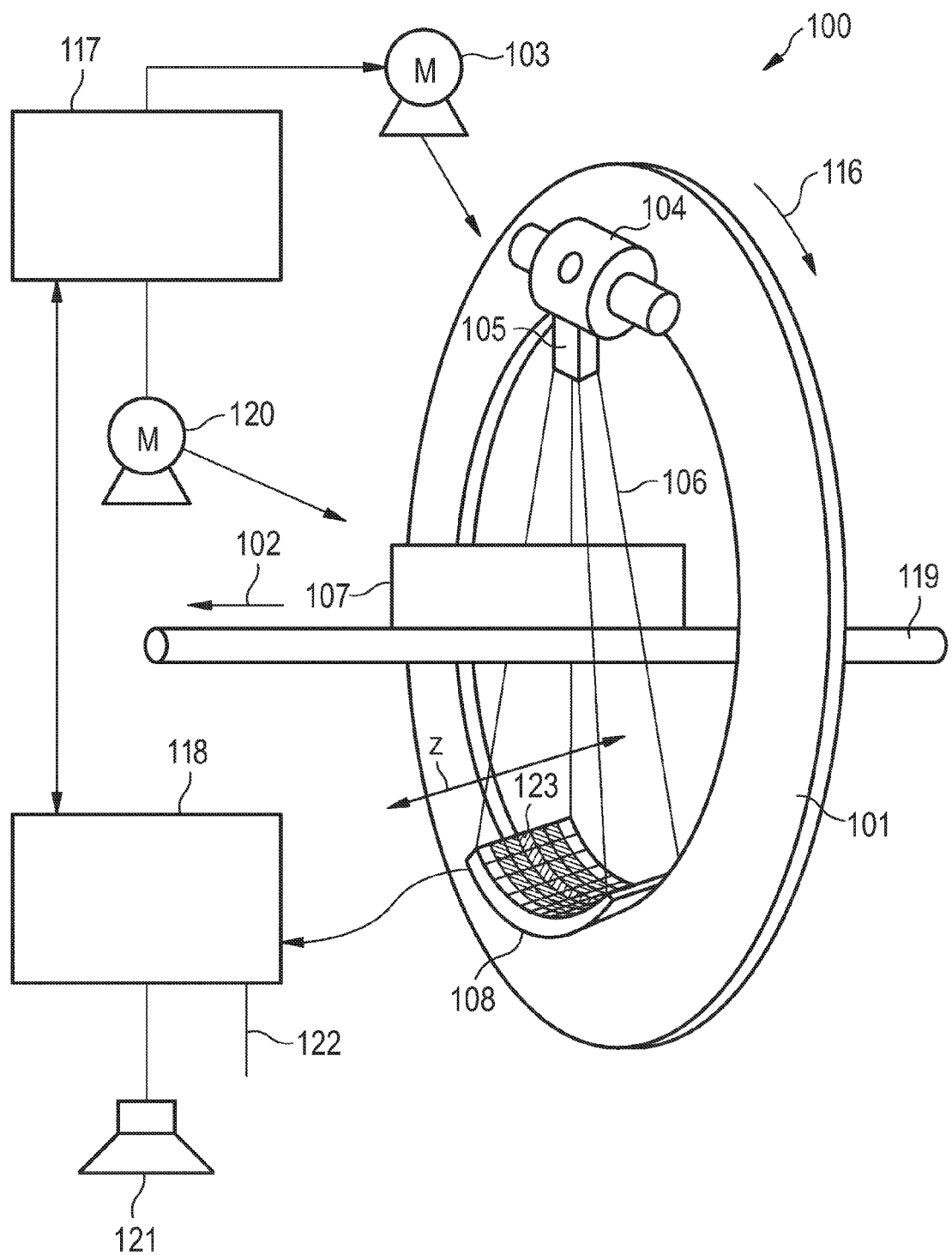
FIG. 1 shows a computer tomography apparatus according to an exemplary embodiment of the present invention.

FIG. 1 shows an exemplary embodiment of a CSCT scanner system according to an exemplary embodiment of the present invention. With reference to this exemplary embodiment, the present invention will be described for the application in baggage inspection to detect hazardous materials, such as explosives, in items of baggage. However, it should be noted that the present invention is not limited to this application, but may also be applied in the field of medical imaging, or other industrial applications, such as material testing.

The computer tomography apparatus 100 depicted in FIG. 1 is a cone-beam CT scanner. However, the invention may also be carried out a with a fan-beam geometry. The CT scanner depicted in FIG. 1 comprises a gantry 101, which is rotatable around a rotational axis 102. The gantry 101 is driven by means of a motor 103. Reference numeral 104 designates a source of radiation such as an X-ray source, which, according to an aspect of the present invention, emits a polychromatic radiation.

Reference numeral 105 designates an aperture system which forms the radiation beam emitted from the radiation source to a cone-shaped radiation beam 106. The cone-beam 106 is directed such that it penetrates an object of interest 107 arranged in the centre of the gantry 101, i.e. in an examination region of the CSCT scanner, and impinges onto the detector 108. As may be taken from FIG. 1, the detector 108 is arranged on the gantry 101 opposite to the source of radiation 104, such that the surface of the detector 108 is covered by the cone-beam 106. The detector 108, which is depicted in FIG. 1, comprises a plurality of detector elements 123 each capable of detecting, in an energy-resolving manner (in the meaning that they comprise a plurality of pixels, wherein each pixel has a certain predetermined energy threshold and is adapted for detecting and counting photons with energies above that certain predetermined energy threshold and, for example, for further detecting and counting photons which energy is below the predetermined energy threshold) X-rays or individual photons which have been coherently scattered by the object of interest 107.

During a scan of the object of interest 107, the source of radiation 104, the aperture system 105 and the detector 108 are rotated along the gantry 101 in the direction indicated by arrow 116. For rotation of the gantry 101 with the source of radiation 104, the aperture system 105 and the detector 108, the motor 103 is connected to a motor control unit 117, which is connected to a calculation or determination unit 118.

In FIG. 1, the object of interest 107 is an item of baggage which is disposed on a conveyor belt 119. During the scan of the object of interest 107, while the gantry 101 rotates around the object of interest 107, for instance an item of baggage, the conveyor belt 119 displaces the object of interest 107 along a direction parallel to the rotational axis 102 of the gantry 101. By this, the object of interest 107 is scanned along a helical scan path. The conveyor belt 119 may also be stopped during the scans to thereby measure signal slices. Instead of providing a conveyor belt 119, for example, in medical applications where the object of interest 107 is a patient, a movable table may be used. However, it should be noted that in all of the described cases it may also be possible to perform a circular scan, where there is no displacement in a direction parallel to the rotational axis 102, but only the rotation of the gantry 101 around the rotational axis 102.

Further, it shall be emphasized that, as an alternative to the cone-beam configuration shown in FIG. 1, the invention may be realized by a fan-beam configuration. In order to generate a primary fan-beam, the aperture system 105 may be configured as a slit collimator.

The detector 108 may be connected to the determination unit 118. The determination unit 118 may receive the detection result, i.e. the read-outs from the detector elements 123 of the detector 108 and may determine a scanning result on the basis of the read-outs. Furthermore, the determination unit 118 communicates with the motor control unit 117 in order to coordinate the movement of the gantry 101 with motors 103 and 120 with the conveyor belt 119.

The determination 118 may be adapted for constructing an image from read-outs of the detector 108 using a statistical method according to an exemplary embodiment of the present invention. A reconstructed image generated by the calculation unit 118 may be output to a display (not shown in FIG. 1) via an interface 122.

The determination unit 118 may be realized by a data processor to process read-outs from the detector elements 123 of the detector 108.

Furthermore, as may be taken from FIG. 1, the determination unit 118 may be connected to a loudspeaker 121, for example, to automatically output an alarm in case of the detection of suspicious material in the item of baggage 107.

The computer tomography apparatus 100 for examination of the object of interest 107 includes the detector 108 having the plurality of detecting elements 123 arranged in a matrix-like manner, each being adapted to detect X-rays coherently scattered from the object of interest 107 in a threshold-based and thus energy-resolved manner. Furthermore, the computer tomography apparatus 100 comprises the determination or reconstruction unit 118 adapted for combining first, second, third and fourth detection data, resulting in an energy-resolved result signal representing the nominal detector cell.

The computer tomography apparatus 100 comprises the X-ray source 104 adapted to emit X-rays to the object of interest 107. The collimator 105 provided between the electromagnetic radiation source 104 and the detecting elements 123 is adapted to collimate an electromagnetic radiation beam emitted from the electromagnetic radiation source 104 to form a cone-beam. Alternatively, not shown in FIG. 1, a slit collimator may be used instead of collimator 105 to produce a fan-beam. The detecting elements 123 form a multi-slice detector array 108. The computer tomography apparatus 100 may be configured as a baggage inspection apparatus.

Figure 2:
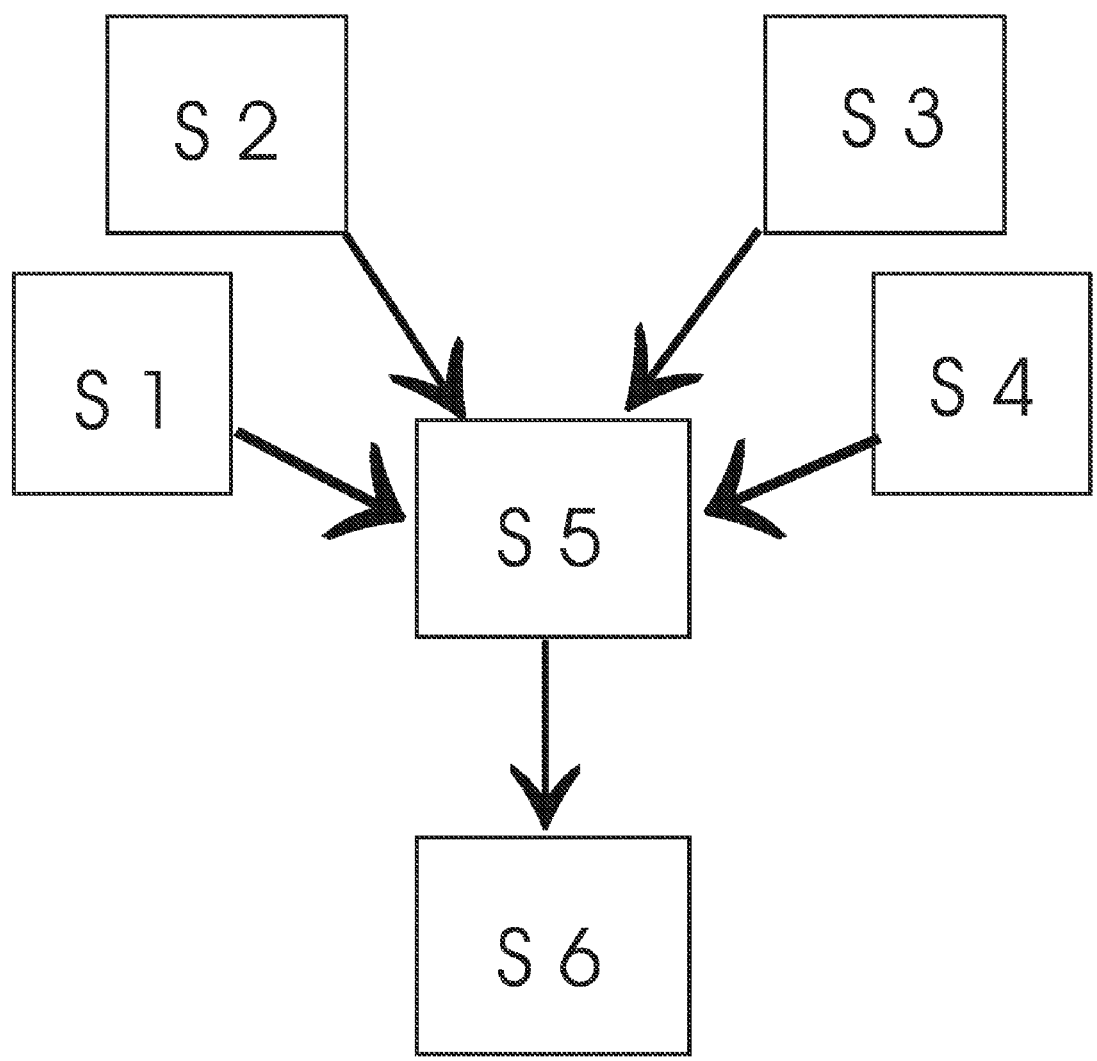
FIG. 2 shows a flow-chart of an exemplary embodiment of a method of examining an object of interest according to the present invention.

In the following, referring to FIG. 2, the method of examining an object of interest according to an exemplary embodiment of the present invention will be described in more detail.

The method starts at step S1-S4, with the acquisition of detection data by a detector element. The detector element may, according to an exemplary embodiment of the present invention, be segmented into a plurality of sub-pixels comprising a first sub-pixel and a second sub-pixel. The first sub-pixel may comprise a first counting channel corresponding to a first energy threshold and a second counting channel corresponding to a second energy threshold. The first counting channel may be adapted for counting detection events or even single photons with an energy above the first threshold energy and the second counting channel may be adapted for counting detection events or even single photons with an energy above the second threshold energy.

In step S1 the photons with energy above the first energy threshold are detected by the first sub-pixel. In step S2 photons with an energy above the second energy threshold are detected by the first sub-pixel.

Furthermore, the detector element comprises a second sub-pixel with a third counting channel corresponding to a third energy threshold and a fourth counting channel corresponding to a fourth energy threshold. The third counting channel is adapted for counting (in step S3) photons or detection events with an energy above the third threshold energy and counting channel four is adapted for counting (in step S4) single photons or detection events corresponding to an energy above the fourth threshold energy.

In other words, each nominal detector cell is segmented into N individual sub-pixels. Each pixel has at least two thresholds and counting channels. The first channel has a low threshold and may therefore count all events. The second channel has a sub-pixel dependent threshold. This dependent threshold varies over the nominal detector cell. For example, sub-pixel n gets threshold $T(n)=E0+n*DE$. Here, E0 is the lowest and $n*DE$ is the highest energy of interest. The results of all sub-pixel channels can be combined to an energy-resolved signal representing the nominal detector cell.

This combination is performed in step S5. In step S5, the determination unit combines the first, second, third and fourth detection data, resulting in an energy-resolved result signal representing the detector element. The result signal may be represented with discrete energy bins. Each sub-pixel may distribute its counts into these bins. The counts that exceed the threshold are equally distributed into the bins representing energy levels above the threshold. The other counts that have been detected only by the low threshold are equally distributed over the other bins.

This may provide for an energy-resolved result signal in step S6.

Further improvements of the energy resolution may be possible by adding further thresholds and counters to a sub-pixel or even to each sub-pixel. The noise statistics of the detector may be improved with a non-linear variation of the threshold within one nominal cell.

It should be noted, that the method may be extended to a more complicated set up of thresholds and offers the possibility to include detector effects in the reconstruction itself.

Segmentation of the detector element into a plurality of sub-pixels may reduce the frequency requirement for each individual channel.

Figure 3:
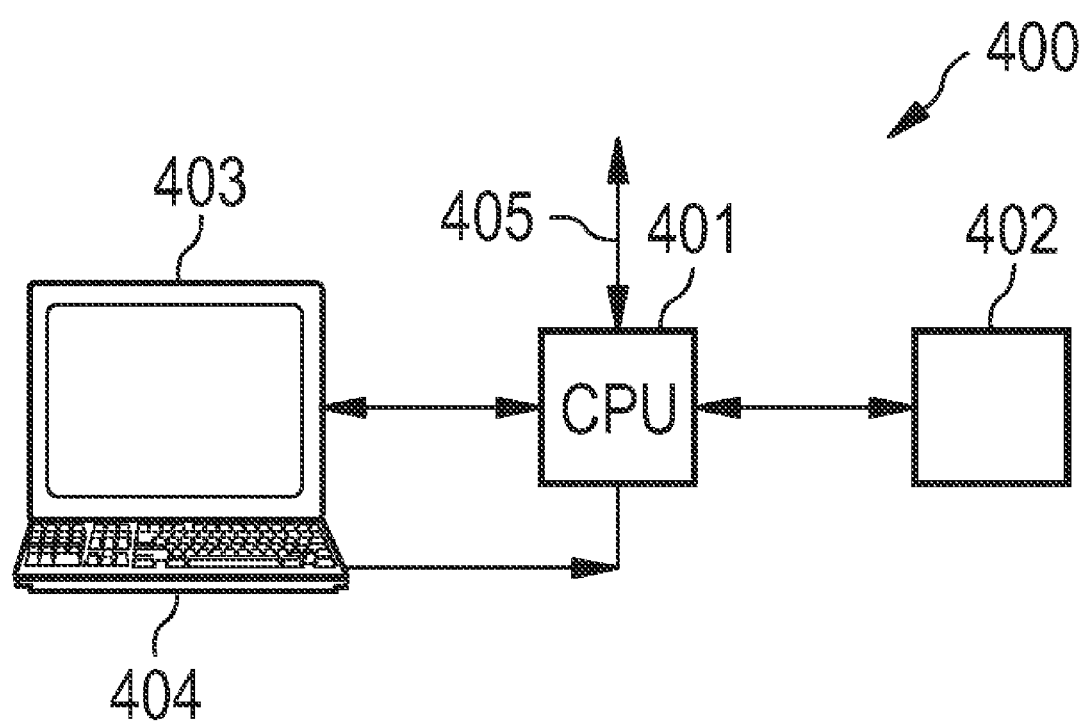
FIG. 3 shows an exemplary embodiment of a data processing device to be implemented in the computer tomography apparatus of the invention.

FIG. 3 depicts an exemplary embodiment of a data processing device 400 according to the present invention for executing an exemplary embodiment of a method in accordance with the present invention. The data processing device 400 depicted in FIG. 3 comprises a central processing unit (CPU) or image processor 401 connected to a memory 402 for storing an image depicting an object of interest, such as a patient or an item of baggage. The data processor 401 may be connected to a plurality of input/output network or diagnosis devices, such as a CT device. The data processor 401 may furthermore be connected to a display device 403, for example, a computer monitor, for displaying information or an image computed or adapted in the data processor 401. An operator or user may interact with the data processor 401 via a keyboard 404 and/or other output devices, which are not depicted in FIG. 3. Furthermore, via the bus system 405, it may also be possible to connect the image processing and control processor 401 to, for example, a motion monitor, which monitors a motion of the object of interest. In case, for example, a lung of a patient is imaged, the motion sensor may be an exhalation sensor. In case the heart is imaged, the motion sensor may be an electrocardiogram.

Exemplary technical fields, in which the present invention may be applied advantageously, include baggage inspection, medical applications, material testing, and material science. An improved image quality and a reduced amount of calculation in combination with a low effort may be achieved. Also, the invention may be applied in the field of heart scanning to detect heart diseases.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. A computer tomography apparatus for examination of an object of interest, the computer tomography apparatus comprising:
   a detector element segmented into a plurality of sub-pixels, the plurality of sub-pixels including at least a first sub-pixel and a second sub-pixel;
   a first counting channel and a second counting channel associated with the first sub-pixel, the first counting channel corresponding to a first x-ray energy threshold and the second counting channel corresponding to a second x-ray energy threshold, which is dependent on first lowest and highest x-ray energies of interest for the first sub-pixel; and
   a third counting channel and a fourth counting channel associated with the second sub-pixel, the third counting channel corresponding to a third x-ray energy threshold and the fourth counting channel corresponding to a fourth x-ray energy threshold, which is dependent on second lowest and highest x-ray energies of interest for the second sub-pixel;
   wherein at least one of the first lowest x-ray energy of interest is different than the second lowest x-ray energy of interest or the first highest x-ray energy of interest is different than the second highest x-ray energy of interest.

2. The computer tomography apparatus of claim 1, wherein the first sub-pixel is adapted for detecting a first x-ray radiation with a first x-ray energy above the first x-ray energy threshold and for detecting a second x-ray radiation with a second x-ray energy above the second x-ray energy threshold, resulting in first and second detection data; and the second sub-pixel is adapted for detecting a third x-ray radiation with a third x-ray energy above the third x-ray energy threshold and for detecting a fourth x-ray radiation with a fourth x-ray energy above the fourth x-ray energy threshold, resulting in third and fourth detection data.

3. The computer tomography apparatus of claim 2, further comprising a determination unit adapted for combining the first, second, third and fourth detection data, resulting in an x-ray energy resolved result signal representing the detector element.

4. The computer tomography apparatus of claim 3, wherein the result signal is represented on the basis of a first, second, third and fourth x-ray energy bin; the first, second, third and fourth x-ray energy bins are discrete x-ray energy bins; the first and third threshold x-ray energies are lower than the second threshold x-ray energy which is lower than the fourth threshold x-ray energy; and the third counts, which result from photons with an x-ray energy above the third threshold x-ray energy, are equally distributed into the third and fourth x-ray energy bins.

5. The computer tomography apparatus of claim 1, wherein the first counting channel is adapted for counting, as first counts, detection events resulting from photons with an x-ray energy above the first threshold x-ray energy; the second counting channel is adapted for counting, as second counts, detection events resulting from photons with an x-ray energy above the second threshold x-ray energy; the third counting channel is adapted for counting, as third counts, detection events resulting from photons with an x-ray energy above the third threshold x-ray energy; and the fourth counting channel is adapted for counting, as fourth counts, detection events resulting from photons with an x-ray energy above the fourth threshold x-ray energy.

6. The computer tomography apparatus of claim 1, wherein the first x-ray energy threshold equals the third x-ray energy threshold; and the second x-ray energy threshold is different from the fourth x-ray energy threshold.

7. The computer tomography apparatus of claim 1, wherein the first and second sub-pixels are adapted for detecting corresponding single photons.

8. The computer tomography apparatus of claim 1, wherein the computer tomography apparatus is adapted as a coherent scatter computer tomography apparatus.

9. The computer tomography apparatus of claim 1, further comprising:
   an x-ray radiation source adapted for emitting x-ray radiation to an object of interest; and
   a collimator arranged between the x-ray radiation source and the detecting elements;
   wherein the collimator is adapted for collimating an x-ray radiation beam emitted by the x-ray radiation source to form a fan-beam or a cone-beam.

10. The computer tomography apparatus of claim 1, wherein the detecting elements form a single-slice detector array.

11. The computer tomography apparatus of claim 1, wherein the detecting elements form a multi-slice detector array.

12. The computer tomography apparatus of claim 1, configured as one of the group consisting of a baggage inspection apparatus, a medical application apparatus, a material testing apparatus and a material science analysis apparatus.

13. The computer tomography apparatus of claim 1, wherein the second x-ray energy threshold is equal to a sum of the lowest x-ray energy of interest and the highest x-ray energy of interest for the first sub-pixel.

14. The computer tomography apparatus of claim 1, wherein the fourth x-ray energy threshold is equal to a sum of the lowest x-ray energy of interest and the highest x-ray energy of interest for the second sub-pixel.

15. A detector for a computer tomography apparatus for examination of an object of interest, the detector comprising:
   a detector element segmented into a plurality of sub-pixels, the plurality of sub-pixels including a first sub-pixel and a second sub-pixel;
   a first counting channel and a second counting channel associated with the first sub-pixel, the first counting channel corresponding to a first x-ray energy threshold and the second counting channel corresponding to a second x-ray energy threshold, which is dependent on first lowest and highest x-ray energies of interest for the first sub-pixel; and
   a third counting channel and a fourth counting channel associated with the second sub-pixel, the third counting channel corresponding to a third x-ray energy threshold and a fourth counting channel corresponding to a fourth x-ray energy threshold, which is dependent on second lowest and highest x-ray energies of interest for the second sub-pixel;
   wherein at least one of the first lowest x-ray energy of interest is different than the second lowest x-ray energy of interest or the first highest x-ray energy of interest is different than the second highest x-ray energy of interest.

16. A method of examining an object of interest with a computer tomography apparatus, the method comprising the steps of:
   detecting, by a first sub-pixel, a first x-ray radiation with a first x-ray energy above a first x-ray energy threshold and a second x-ray radiation with a second x-ray energy above a second x-ray energy threshold, which is dependent on first lowest and highest x-ray energies of interest for the first sub-pixel, resulting in first and second detection data; and
   detecting, by a second sub-pixel, a third x-ray radiation with a third x-ray energy above a third x-ray energy threshold and a fourth x-ray radiation with a fourth x-ray energy above a fourth x-ray energy threshold, which is dependent on second lowest and highest x-ray energies of interest for the second sub-pixel, resulting in third and fourth detection data;
   wherein the first sub-pixel includes a first counting channel corresponding to the first x-ray energy threshold and a second counting channel corresponding to the second x-ray energy threshold, and the second sub-pixel includes a third counting channel corresponding to the third x-ray energy threshold and a fourth counting channel corresponding to the fourth x-ray energy threshold; and at least one of the first lowest x-ray energy of interest is different than the second lowest x-ray energy of interest or the first highest x-ray energy of interest is different than the second highest x-ray energy of interest.

17. The method of claim 16, wherein the second x-ray energy threshold is equal to a sum of the lowest x-ray energy of interest and the highest x-ray energy of interest for the first sub-pixel.

18. The method of claim 16, wherein the fourth x-ray energy threshold is equal to a sum of the lowest x-ray energy of interest and the highest x-ray energy of interest for the second sub-pixel.

19. A computer-readable medium, in which a computer program of examining an object of interest with a computer tomography apparatus is stored which, when being executed by a processor, is adapted to carry out the steps of:
   detecting, by a first sub-pixel, a first x-ray radiation with a first x-ray energy above a first x-ray energy threshold and a second x-ray radiation with a second x-ray energy above a second x-ray energy threshold, which is dependent on first lowest and highest x-ray energies for the first sub-pixel, resulting in first and second detection data; and
   detecting, by a second sub-pixel, a third x-ray radiation with a third x-ray energy above a third x-ray energy threshold and a fourth x-ray radiation with a fourth x-ray energy above a fourth x-ray energy threshold, which is dependent on second lowest and highest x-ray energies of the second sub-pixel, resulting in third and fourth detection data;
   wherein the first sub-pixel includes a first counting channel corresponding to the first x-ray energy threshold and a second counting channel corresponding to the second x-ray energy threshold, and the second sub-pixel includes a third counting channel corresponding to the third x-ray energy threshold and a fourth counting channel corresponding to the fourth x-ray energy threshold; and at least one of the first lowest x-ray energy of interest is different than the second lowest x-ray energy of interest or the first highest x-ray energy of interest is different than the second highest x-ray energy of interest.

* * * * *